United States Patent [19]

Moaddeb

[11] Patent Number: 5,154,182

[45] Date of Patent: Oct. 13, 1992

[54] DRUG OR STEROID RELEASING PATCH ELECTRODE FOR AN IMPLANTABLE ARRHYTHMIA TREATMENT SYSTEM

[75] Inventor: Shawn Moaddeb, Woodland Hills, Calif.

[73] Assignee: Siemens Pacesetter, Inc., Sylmar, Calif.

[21] Appl. No.: 656,345

[22] Filed: Feb. 15, 1991

[51] Int. Cl.$^5$ .............................................. A61N 1/05
[52] U.S. Cl. ..................................... 128/784; 128/642
[58] Field of Search ........................ 128/642, 784, 785

[56] References Cited

U.S. PATENT DOCUMENTS

| | | | |
|---|---|---|---|
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,711,251 | 12/1987 | Stokes | 128/784 |
| 4,819,661 | 4/1989 | Heil, Jr. et al. | 128/786 |
| 4,819,662 | 4/1989 | Heil, Jr. et al. | 128/786 |
| 4,922,926 | 5/1990 | Hirschberg et al. | 128/785 |
| 4,938,231 | 7/1990 | Milijasevic et al. | 128/785 |

Primary Examiner—William E. Kamm
Assistant Examiner—Scott M. Getzow
Attorney, Agent, or Firm—Leslie S. Miller; Malcolm J. Romano

[57] ABSTRACT

A patch electrode of the type which is surgically attached to the epicardium for use in an implantable arrhythmia treatment system is disclosed which has one or more regions of exposed electrode mesh on a side of the electrode in direct contact with the epicardium. The mesh is held in a flexible carrier having a periphery between the exposed mesh and the edge of the carrier. A layer of a drug or steroid is carried on the carrier in this peripheral region, the drug or steroid interacting with body fluid and thereby slowly releasing into the surrounding tissue. The drug or steroid may be selected to provide antiarrhythmia therapy, reduce inflammation, retard tissue growth or may be an antimicrobial drug. The layer carried on the carrier may be on surface thereof, contained in a shallow trough in the carrier, or impregnated within the carrier material. The layer may be carried on one or both sides of the carrier.

8 Claims, 1 Drawing Sheet

DRUG OR STEROID RELEASING PATCH ELECTRODE FOR AN IMPLANTABLE ARRHYTHMIA TREATMENT SYSTEM

BACKGROUND OF THE INVENTION

1. Field of the Invention

The present invention relates generally to a patch electrode of the type used in an implantable arrhythmia treatment system, and more particularly to such an electrode for releasing a drug or steroid at the site of implantation of the electrode.

2. Description of the Prior Art

The use of steroids and drugs released internally in vivo for treating various types of cardiac disorders is well known. The use of such drugs is known to treat naturally occurring cardiac pathologies, as well as to counter trauma which is caused by the implantation of a cardiac assist device, such as a cardiac pacemaker. Such trauma typically occurs in the region of attachment of the distal end of the pacing lead or leads to the cardiac tissue.

For example, pacing leads which are anchored in the heart by means of tines at a distal end thereof which engage the trabeculae and which have a cavity at the distal end of the lead in which a drug to counter undesirable interactions between the lead and tissue is contained, are disclosed in U.S. Pat. No. 4,711,251, to Stokes, and in U.S. Pat. No. 4,506,680, also to Stokes. Tined leads having tips consisting of porous or molecular sieve-forming material, with a drug being stored in and dispensed from the tip, are disclosed in U.S. Pat. No. 4,819,662, to Heil, Jr. et al.; in U.S. Pat. No. 4,606,118, to Cannon et al.; and in U.S. Pat. No. 4,577,642, to Stokes.

A screw-in pacemaker lead is disclosed in U.S. Pat. No. 4,819,661, to Heil, Jr. et al., which has a chamber open to the distal end of the lead. A matrix impregnated with a therapeutic drug is retained in the chamber.

In addition to implantable devices intended to assist cardiac pacing, implantable devices are known which are intended to treat various types of cardiac arrhythmia. Such devices deliver electrical energy to the cardiac muscle at much higher energies than are typically used for cardiac pacing. Such implantable systems may be used to deliver defibrillation pulses to counter ventricular fibrillation, and may also be capable of delivering therapeutic cardioversion lower energy pulses to treat other types of arrhythmia, such as atrial fibrillation, atrial flutter, and tachycardia. Such known implantable systems may include sensors and processing circuitry which identify the type of arrhythmia which is present, and select an appropriate treatment in the form of one or more pulses of the appropriate energy.

Because of the higher energies which are needed to defibrillate or cardiovert, the pulses generated by implantable arrhythmia treatment systems cannot be delivered to the cardiac muscle with an electrode comparable to a low-energy pacing electrode, because the electrical current density at the pulse delivery site would be so high as to cause significant damage to the surrounding cardiac tissue. Typically, therefore, implantable arrhythmia systems employ a patch electrode so that the electrical energy may be distributed over a larger delivery site, thereby reducing the current density to a tolerable level. Because of the different structure of such patch electrodes, drug delivery and releasing techniques and structures of the type used in cardiac pacing leads cannot be used in such patch electrodes.

SUMMARY OF THE INVENTION

It is an object of the present invention to provide a patch electrode of the type used in an implantable arrhythmia treatment system which includes means for releasing a drug or steroid at the implantation site of the patch electrode.

The above object is achieved in accordance with the principles of the present invention in a patch electrode having electrode material contained within a flexible carrier, with the carrier having openings therein so that the electrode material is directly exposable to cardiac tissue when the electrode is implanted. The flexible material of the carrier forms a peripheral region between the edges of the open region and the outer edges of the carrier, with a layer of a drug or steroid being carried on the carrier at this peripheral region. The drug or steroid may be contained, for example, in a matrix of the type which slowly dissolves upon interaction with body fluid, thereby releasing the drug or steroid into the surrounding tissue at the attachment site of the patch electrode.

As used herein, the term "carried on" as applied to the drug or steroid being carried on the carrier means that the layer containing the drug or steroid alternately may be applied on the surface of the carrier, contained in a shallow trough in the surface of the carrier, or directly impregnated into the carrier material.

The drug or steroid layer is preferably disposed on the side of the patch electrode which is in direct contact with the cardiac tissue when the electrode is implanted. However, the layer may alternatively or additionally be disposed on the side of the patch electrode facing away from the cardiac tissue.

DESCRIPTION OF THE PREFERRED EMBODIMENTS

Figure 1:
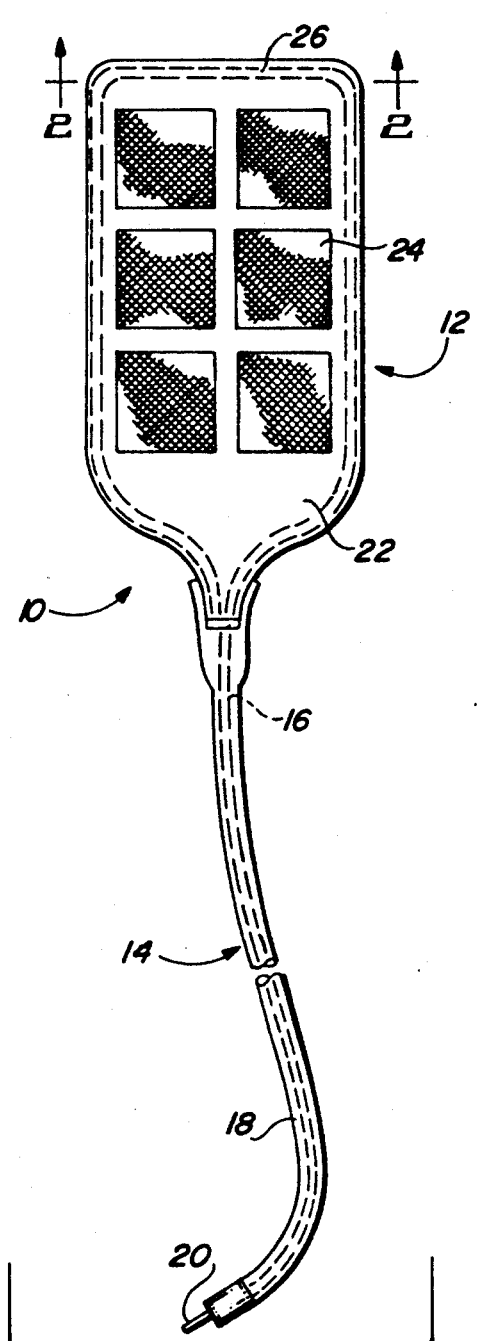
FIG. 1 is a plan view of a patch electrode constructed in accordance with the principles of the present invention.

A patch electrode 10 constructed in accordance with the principles of the present invention, and being of the type suitable for use in an implantable arrhythmia treatment system, is shown in FIG. 1. The patch electrode 10 generally consists of an energy delivery portion 12 and an energy supply portion 14. The energy supply portion 14 is in the form of a standard implantable cable having one or more electrical conductors 16 contained in a flexible insulating coating 18, the flexible insulating coating 18 consisting of material which is inert to body fluids. The free end of the energy supply portion 14 terminates in one or more connector terminals 20, adapted to be electrically and mechanically connected to an implantable pulse generator (not shown) of an arrhythmia treatment system.

The energy delivery portion 12 generally consists of a mesh electrode 24 contained in a flexible carrier 22. The flexible carrier 22 may consist, for example, of silicone-based material. The mesh electrode 24 is electrically connected to the conductor or conductors 16 in a known manner (not shown). The mesh electrode 24 is completely covered by the flexible carrier 22, except for one or more exposed regions. In the exemplary embodiment shown in FIG. 1, these exposed regions are shown in the form of a plurality of generally quadratic openings in the flexible carrier 22. However, it will be understood that other shapes and configurations of patch electrodes may be used without departing from the inventive concepts disclosed herein.

In accordance with the principles of the present invention, a peripheral region of the flexible carrier 22 between an edge of the openings exposing the mesh electrode 24 and the edge of the flexible carrier 22, is provided with a drug or steroid layer 26 extending substantially continuously around the entirety of this peripheral region. The face or surface of the patch electrode 10 which is visible in FIG. 1 is the surface which is intended for direct contact with the cardiac tissue when the patch electrode is implanted.

The drug or steroid layer 26 may be a matrix of the type which is known to those skilled in the art which contains the drug or steroid and which slowly dissolves upon interaction with body fluids, thereby releasing the drug or steroid into the surrounding tissue. The drug may be of the type known to reduce defibrillation threshold (DFT). The drug may be an arrhythmia therapy medication, an anti-microbial drug, or a tissue growth retardant. The use of a steroid or steroid-based drug will reduce inflammation which may occur at the attachment site at the time of implantation of the patch electrode, particularly at the locations at which the patch electrode 10 is sutured to the heart.

Figure 2:
FIG. 2 is a sectional view of the electrode of FIG. 1.
Figure 3:
FIG. 3 is a sectional view at the same location in a patch electrode as shown in FIG. 2, showing a first further embodiment of the electrode.

As shown in FIG. 2, the drug or steroid layer 26 in the embodiment of FIG. 1 is carried on the flexible carrier 22 as a layer applied to the surface of the flexible carrier 22. As shown in the first alternate embodiment of FIG. 3, however, the flexible carrier 2 may be provided with a shallow trough 27 in which a drug or steroid layer 28 may be contained so that the top of the drug or steroid layer 28 is substantially flush with the surface of the flexible carrier 22.

Figure 4:
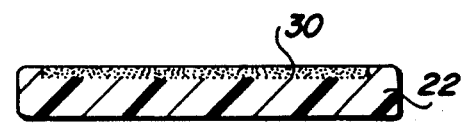
FIG. 4 is a sectional view at the same location in a patch electrode as shown in FIG. 2, showing a second further embodiment of the electrode.

A second alternate embodiment is shown in FIG. 4, wherein a drug or steroid layer 30 is carried on the flexible carrier 22 in the form of a layer directly impregnated into the material of the flexible carrier 22. Such impregnation may be accomplished, for example, by injecting the drug or steroid into the flexible carrier 22 after the flexible carrier 22 has been manufactured, or impregnation of the drug or steroid may be undertaken integrated with the manufacture of the flexible carrier 22 itself.

Figure 5:
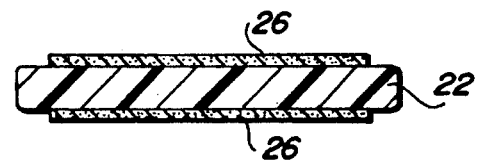
FIG. 5 is a sectional view taken at the same location in a patch electrode as shown in FIG. 2, showing a third further embodiment of the patch electrode.

As shown in the third alternate embodiment of FIG. 5, the drug or steroid layer 26 may be carried on both sides of the flexible carrier 22. Although FIG. 5 involves a variation of the embodiment of FIG. 2, it will be understood that in the embodiments of FIGS. 3 and 4, the layers 28 or 30 could be carried on both sides of the flexible carrier 22 as well. It will also be understood that the layer 26 (or 28 or 30) may be disposed only on the side of the flexible carrier 22 facing away from the cardiac tissue, when implanted, which is the bottom of the carrier shown in FIG. 5.

Although modifications and changes may be suggested by those skilled in the art, it is the intention of the inventor to embody within the patent warranted hereon all changes and modifications as reasonably and properly come within the scope of his contribution to the art.

What is claimed is:

1. A patch electrode for use in an implantable arrhythmia treatment system comprising:
   a carrier containing electrode mesh adapted to be attached in vivo to cardiac tissue for delivery of therapeutic electrical energy to said cardiac tissue, said carrier having a first surface adapted to be in direct contact with said cardiac tissue when said carrier is implanted and a second surface adapted to face away from said cardiac tissue when said carrier is implanted; and
   a therapeutic drug carried on both of said first and second surfaces of said carrier for interacting with said cardiac tissue after implantation of said carrier.

2. A patch electrode, as claimed in claim 1, wherein said therapeutic drug is carried on said carrier as a layer on at least one surface of said carrier.

3. A patch electrode, as claimed in claim 1, wherein said carrier has a shallow trough in at least one surface thereof, and wherein said therapeutic drug is carried on said carrier in said trough.

4. A patch electrode, as claimed in claim 1, wherein said therapeutic drug is carried on said carrier as a layer impregnated in at least one surface of said carrier.

5. A patch electrode for use in an implantable arrhythmia treatment system comprising:
   a carrier having a surface thereof adapted for direct contact with cardiac tissue when said carrier is implanted, said carrier having another surface thereof adapted to face away from said cardiac tissue when said carrier is implanted, at least one of said surfaces having at least one opening therein;
   an electrode mesh contained within said carrier and exposed for direct contact with said cardiac tissue through said at least one opening in said carrier, said carrier having a peripheral region between said at least one opening and an edge of said carrier; and
   a therapeutic drug layer carried on each surface of said carrier in said peripheral region thereof.

6. A patch electrode, as claimed in claim 5, wherein said therapeutic drug layer is carried on said carrier as a layer on at least one surface of said carrier.

7. A patch electrode, as claimed in claim 5, wherein said carrier has a shallow trough in at least one surface thereof, and wherein said therapeutic drug layer is carried on said carrier in said trough.

8. A patch electrode, as claimed in claim 5, wherein said therapeutic drug layer is carried on said carrier as a layer impregnated in at least one surface of said carrier.

* * * * *